United States Patent [19]

Culver et al.

[11] Patent Number: 5,445,160
[45] Date of Patent: Aug. 29, 1995

[54] PORTABLE CARBON DIOXIDE MONITOR

[75] Inventors: John A. Culver, San Francisco; Ross F. Flewelling, Oakland; John M. Farbarik, Hayward; Charles E. Stuart, San Jose; James M. Davenport, Fallbrook, all of Calif.

[73] Assignee: Nellcor Incorporated, Pleasanton, Calif.

[21] Appl. No.: 82,329

[22] Filed: Jun. 24, 1993

Related U.S. Application Data

[63] Continuation of Ser. No. 831,126, Feb. 4, 1992, abandoned, which is a continuation-in-part of Ser. No. 697,133, May 8, 1991, abandoned.

[51] Int. Cl.6 .............................................. A61B 5/08
[52] U.S. Cl. ................................. 128/719; 128/205.23; 128/207.14
[58] Field of Search ............. 128/719, 202.22, 205.23, 128/207.14, 207.15

[56] References Cited

U.S. PATENT DOCUMENTS

| | | | |
|---|---|---|---|
| 3,826,918 | 7/1974 | Van Der Koogh et al. | 250/343 |
| 3,913,379 | 10/1975 | Rusz et al. | 73/27 R |
| 4,011,859 | 3/1977 | Frankenberger | 128/2 C |
| 4,417,589 | 11/1983 | Favaloro | 128/716 |
| 4,485,822 | 12/1984 | O'Connor et al. | 128/719 |
| 4,537,190 | 8/1985 | Caillot et al. | 128/205.23 |
| 4,648,396 | 3/1987 | Raemer | 128/719 |
| 4,914,720 | 4/1990 | Knodle et al. | 250/343 |
| 4,928,703 | 5/1990 | Wong | 128/719 |
| 4,955,946 | 9/1990 | Mount et al. | 128/719 |
| 4,958,075 | 9/1990 | Mace et al. | 250/343 |
| 5,005,573 | 4/1991 | Buchanan | 128/207.14 |
| 5,067,492 | 11/1991 | Yelderman et al. | 128/719 |
| 5,081,998 | 1/1992 | Yelderman et al. | 128/719 |
| 5,095,900 | 3/1992 | Fertig et al. | 128/719 |
| 5,153,427 | 10/1992 | Takahashi et al. | 250/231.1 |

OTHER PUBLICATIONS

"Tri Med 510 CO2 Respiration Monitor" advertisement from *Anesthesiology* (Jun. 1984).

Primary Examiner—Edgar S. Burr
Assistant Examiner—Aaron J. Lewis
Attorney, Agent, or Firm—Townsend and Townsend Khourie and Crew

[57] ABSTRACT

A $CO_2$ monitor which has a reusable portion and a disposable portion is disclosed. The disposable portion includes an airway sensor for connecting between a ventilator output and an endotracheal tube. The airway sensor has ports on opposite sides. In one port a disposable infrared light source is inserted with wire contacts extending to the exterior of the airway sensor body. The reusable portion is a detector module which includes a detector and an amplifier. The detector module attaches to the airway sensor so that the detector is disposed in the second port and so that contacts in the detector module communicate with the wire contacts of the light source. The detector module may be removed from the airway sensor without removing the light source from the airway sensor.

23 Claims, 3 Drawing Sheets

PORTABLE CARBON DIOXIDE MONITOR

This is a continuation of application Ser. No. 07/831,126 filed Feb. 4, 1992, now abandoned which is a continuation-in-part of application Ser. No. 07/697,133, filed May 8, 1991, now abandoned.

BACKGROUND

This invention relates generally to gas analysis devices, specifically to the detection and monitoring of carbon dioxide gas through the use of non-dispersive infrared optical technology. The primary intended applications are the verification of proper intubation, assessment of the adequacy of ventilation (as in CPR), and the detection of cessation of respiratory activity (apnea).

Mechanical ventilating machines and hand bagging techniques both pump respiratory gases to and from a patient through an endotracheal tube that has been inserted into the patient's trachea. The ventilator output port is typically a plastic tube that slides onto the end of the endotracheal tube.

Prior art respiratory carbon dioxide analyzers generally fall into one of two categories. The first category is a sidestream system that extracts gas samples from the endotracheal tube and passes the sample through an optical cell within the instrument. The second category is a mainstream system with a precisely-dimensioned optical cell inserted directly in the flow path between the ventilator and the endotracheal tube. The output of both types of prior art analyzers is a precise indication of the shape and duration of the optical waveform and, in some, a precise measurement of carbon dioxide concentration in the respiratory gas.

U.S. Pat. No. 4,648,396, shows a system with an infrared source and an infrared detector mounted in two heads of a clothespin type clip-on device. The device clips onto a special Y-shaped connector which connects between the endotracheal tube, a source of inspired gas and a receptacle for expired gas. Recesses are provided in the Y connector for mating with the clothespin heads. This system, like other prior art systems, utilizes the fact that carbon dioxide absorbs infrared radiation at a wavelength of approximately 4.25 microns. However, this system provides only a qualitiative indication of relative changes in carbon dioxide concentration in the airway. Other related systems are shown in U.S. Pat. Nos. 4,417,589; 4,537,190; 4,938,703; 3,826,918; and 4,914,720.

One problem with measuring the gas content for a particular patient is that of contamination of the sensor. The invention disclosed in U.S. Pat. No. 4,648,396 avoids this problem by having the clothespin sensor clip on to the outside of a special Y-shaped connector with the Y-shaped connector having windows for the passage of infrared radiation. Thus, the sensor never comes in contact with the patient's breath. U.S. Pat. No. 3,826,918 shows the use of a porous window with purging fluids to avoid contamination. U.S. Pat. No. 4,914,720 shows in FIG. 8 a disposable plastic adapter with sapphire windows. The adapter is placed in the gas monitoring system of FIG. 2 with infrared radiation being projected through the sapphire windows.

SUMMARY OF THE INVENTION

The present invention provides a semi-quantitative carbon dioxide monitor which has a reusable portion and a disposable portion. The disposable portion is an airway sensor for connecting between a ventilator output and an endotracheal tube. The airway sensor housing has ports on opposite sides. In one port a disposable infrared light source is inserted with wire contacts extending to the exterior of the airway sensor housing. The reusable portion is a detector module including a detector, an amplifier, and a cable for connecting the detector and the light source to a monitor. When the detector module is attached to the airway sensor, the detector is disposed in the second port, and a pair of conductors in the cable makes contact with the light source's electrical contacts.

The reusable detector module is connected by a cable to a monitor which includes circuitry for analyzing the waveform from the photodetector output (which corresponds to changes in the carbon dioxide content of the air passing through the airway sensor) to determine if the patient is breathing. The peaks and troughs of the waveform are compared to a threshold computed from historical averages of waveform minimums and maximums to determine whether a wave form cycle is likely to be caused by a breath. The waveform is then qualified as a breath if certain arbitary waveform period and peak value criteria are satisfied. A semi-quantitative display of carbon dioxide concentration is provided by a segmented "blip bar" display on the monitor. Both audible and visual alarms are provided if breathing ceases.

For a fuller understanding of the nature and advantages of the invention, reference should be made to the ensuing detailed description taken in conjunction with the accompanying drawings.

DETAILED DESCRIPTION OF THE PREFERRED EMBODIMENTS

Figure 1:
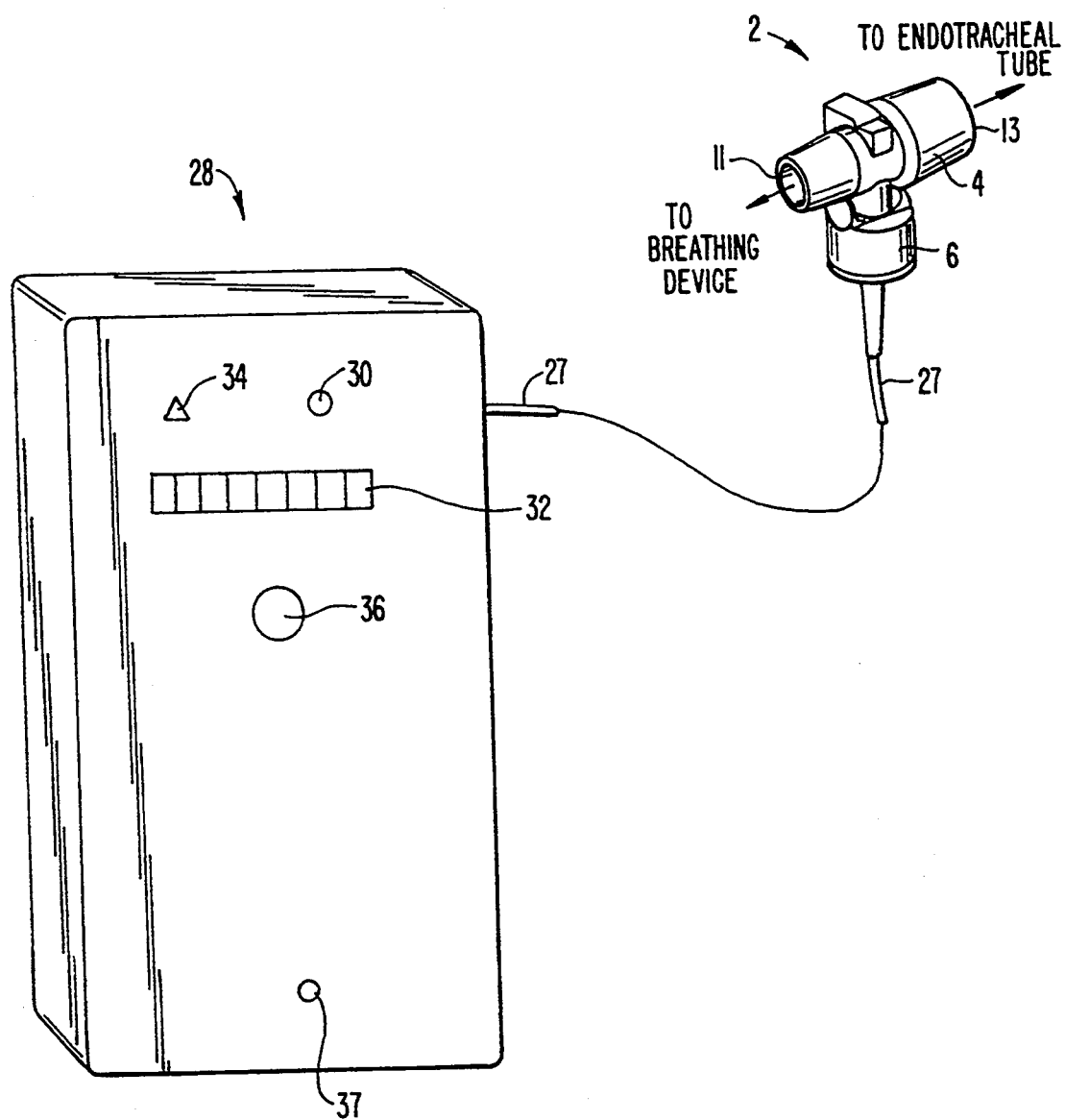
FIG. 1 shows a system according to a preferred embodiment of the present invention.
Figure 2:
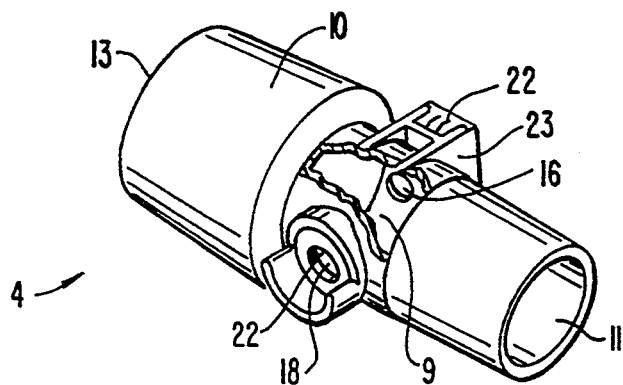
FIG. 2 shows a partial cutaway view of the airway sensor of the system of FIG. 1.
Figure 3:
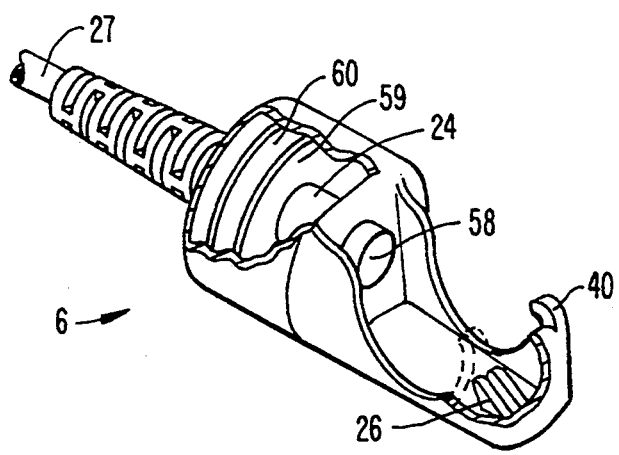
FIG. 3 shows a partial cutaway the detector module of the system of FIG. 1.

FIGS. 1-3 show a respiratory carbon dioxide detection and monitoring system. Carbon dioxide detector unit 2 consists of an airway sensor 4 and a detachable detector module 6. Airway sensor 4 has a housing 10 defining a sensor chamber 9 and an air passageway therethrough. At one end of the air passageway is a respirator port 11 connected to a tube (not shown) leading to a respirator device (such as a mechanical ventilator or anesthesia machine), and at the other end of the air passageway is a patient port 13 connected to a tube (such as an endotracheal tube) (not shown) leading to a patient. In the preferred embodiment, housing 10 is made from polypropylene.

A light port 16 and a detector port 18 are formed in housing 10 on opposite sides of sensor chamber 9. Port 16 and port 18 define an optical path of predetermined length across sensor chamber 9 for the optical detection of carbon dioxide flowing through the air passageway as discussed below.

Figure 4A:
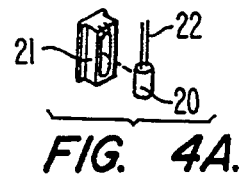
FIG. 4 shows the light source element of the airway sensor of FIGS. 1 and 2.
Figure 4B:
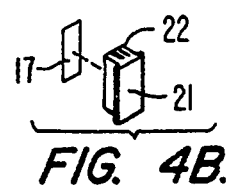
Figure 4C:
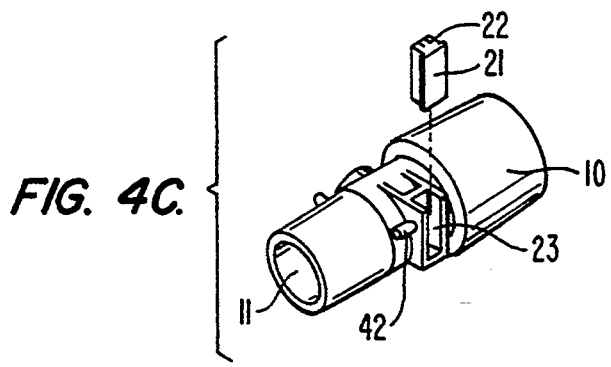

As shown in FIG. 4(a), an infrared light source 20 is preferably mounted in a casing 21 and covered by a transparent membrane 17 made from 0.001 inch polypropylene. The light source is preferably an incandescent broad band lamp, model OL-3070, manufactured by Oshino Lamps (5 Volt, T1, ⅛" bulb), although any light source with substantial emissions in the infrared band may be used. A pair of wires 22 extend from lamp 20 and are bent over the end of casing 21 as shown in FIG. 4(b). Casing 21 fits in a slot 23 formed on the exterior of housing 10 so that the light emitted by source 20 is transmitted along the optical path between port 16 and port 18 and so that wires 22 are exposed to the exterior of housing 10. Once in place, casing 23 is sonically welded to housing 10. A second transparent polypropylene membrane 22 is disposed in housing 10 to seal port 18, as shown in FIG. 2.

Detachable detector module 6 is preferably U-shaped with a photodetector 24 disposed in one arm and a pair of contacts 26 disposed in the other. A pair of conductors (not shown) lead from contacts 26 to a cable 27. Photodetector 24 is preferably a 2 mm by 2 mm lead selenide detector (available from OptoElectronics) mounted in a TO-5 can. A narrow bandpass interference filter 58 is disposed on the open end of the can. Filter 58 is preferably a 4.26 micron wavelength filter with a full width at half maximum of 2%. Carbon dioxide absorbs light at this wavelength. Photodetector 24 is mounted on circuit board 59 disposed in detector module 6.

Two-stage high gain preamplifiers are mounted on circuit board 60 in detector module 6. In the preferred embodiment, a Texas Instruments TL032 op amp is used for the amplifiers.

Detector module 6 attaches to airwary sensor 4 in a snap fit arrangement. A pair of hooks 40 (only one of which is shown in the partial cutaway view of FIG. 3) attach to a pair of ribs 42 on airway sensor housing 10 to align photodetector 24 with port 18 along the optical path and to place contacts 26 against lamp wires 22. When attached in this manner, cable 27 can provide power to lamp 20 and can retrieve the amplified signal from photodetector 24, as discussed below. When the system is to be used on a new patient, detector module 6 may be removed from airway sensor 4 without removing lamp 20 from the airway sensor. Airway sensor 4 may then be disposed of and detector module 6 may be reused.

As seen in FIG. 1, cable 27 leads from detector module 6 to a monitor 28 to provide power for light source 20 and to transmit the signal from detector module 6. Monitor 28 contains the electronics for driving the lamp and for monitoring and interpreting the detector signals. A green light 30 indicates that the patient is breathing. A "blip bar" display 32 of eight LEDs will light up with each breath, with the number of LEDs lighting up indicating the amount of $CO_2$ in the exhalation. A red light 34 will be illuminated if no breath is detected, and at the same time an audible alarm will be sounded through a speaker (not shown) to indicate that the patient has stopped breathing or that the tube has become dislodged. The alarm may be silenced for 60 seconds by depressing button 36. A light 37 may be provided to indicate a low battery condition.

Figure 5:
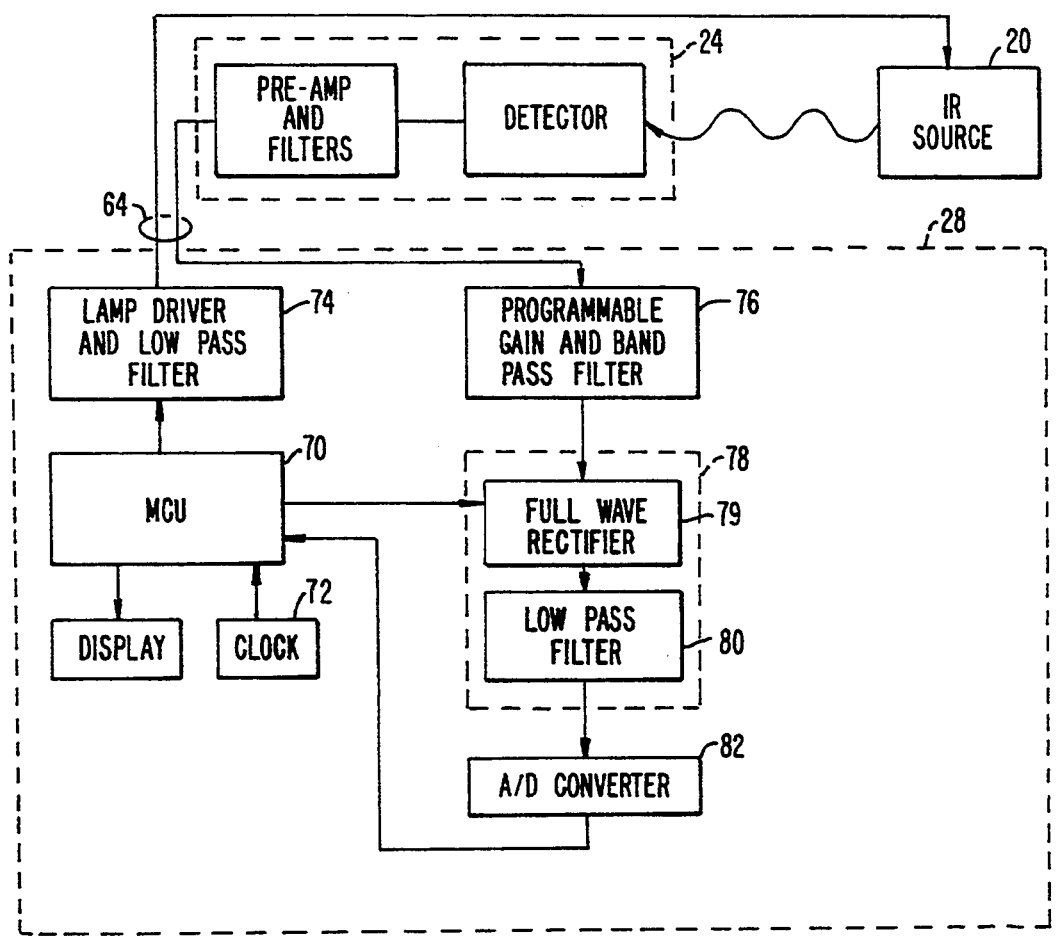
FIG. 5 is a block diagram of all the electronic circuits of FIG. 1.

FIG. 5 shows the overall electronics of the system. Monitor 28 is controlled by a processor, which in the preferred embodiment is a Philips 80C552 microcontroller unit (MCU) 70. MCU 70 is driven by a 16 MHz clock 72. MCU 70 drives light source 20 through a lamp driver 74. The system is powered by 4 "C" batteries.

In order to save on circuitry, the pulse width modulator port (PWM) of MCU 70 provides a 2 KHz signal at a specified duty cycle to drive the lamp. By selecting the appropriate duty cycle, the intensity of the lamp can be controlled by the MCU to adjust the signal level if necessary, as discussed below.

In order to account for DC drift in the photodetector, this system is chopper stabilized, a technique well known in the art. MCU 70 switches on and off the 2 KHz signal at a rate of 36.5 Hz to create a carrier for the modulating light signal received by the detector, and a low pass filter in lamp driver 74 filters out the 2 KHz signal. Comparisons between the voltage levels for light and no light can thus be made in order to compensate for the DC drift of the detector. This electrical pulsing of the lamp is done in lieu of inserting a mechanical chopper wheel in front of the lamp to block and unblock the light between solid and open portions of the chopper wheel. Thus, the present invention eliminates the need for a chopper wheel, making the sensor and detector smaller, lighter, and less prone to failure due to mechanical shocks and vibration, such as being dropped. Good light and dark states are obtained through the use of a bulb with a small, thin filament that can respond rapidly to the current being switched on and off. Such filaments are generally subject to short lifetimes, but the disposable nature of the adapter makes this less of a concern.

Because carbon dioxide absorbs infrared light in the wavelength range passed by IR filter 58, the presence of carbon dioxide in the optical path between light source 20 and photodetector 24 will diminish the amount of light received by photodetector 24. This effect is maximized by IR filter 28 in photodetector 24. Thus, when airway sensor 4 is attached to a patient's endotracheal tube, breath to breath changes in the carbon dioxide concentration in the adapter will modulate the amplitude of the 36.5 Hz carrier received by photodetector 24.

The amplitude modulated carrier is sent from detector module 6 to a programmable gain and band pass filter circuit 76 in monitor 28. The programmable gain is provided to adjust the signal in case there is some blockage or occlusion in the adapter preventing light from substantially getting through. The band pass filter separates the modulated carrier from the noise components at higher and lower frequencies.

The amplitude modulated carrier is then passed through an amplitude demodulator 78, which is clocked by the MCU to alternately invert half cycles. Amplitude demodulator 78 comprises a full wave rectifier 79 and a low pass filter 80. Full wave rectifier 79 produces an all positive signal. Low pass filter 80 then provides the modulating signal (minus the 36.5 Hz carrier) to an analog-to-digital converter 82. Preferably, low pass filter 80 is an approximately 2.5 Hz low pass filter. A Butterworth fourth order low pass filter is used. In the preferred embodiment, the lamp driver duty cycle starts at 100%. If, however, the lamp intensity is so bright that the output of low pass filter 80 exceeds the input range of A/D converter 82, MCU 70 lowers the duty cycle to bring the signal back into range.

MCU 70 passes the digitized signal through a boxcar filter. This is a digital filter which continually sums the latest N sample values, and divides by N to provide an average value. In the preferred embodiment, N is 8.

After filtering, the digitized signal is processed (1) to semiquantitatively display changes in the carbon dioxide concentration in the airway sensor, and (2) to determine whether the time variations in the signal are likely to be caused by the patient's breathing. Assuming that the carbon dioxide concentration in inspired air is negligible, the filtered A/D converter output during inspiration establishes the baseline of the blip bar, i.e., the condition in which only one LED is lit. Theoretically, this "inspired plateau" is a constant number. The actual digitized output may vary, however, due to the presence of noise. The monitor therefore uses a common slope detection algorithm to identify the "flat" portions (i.e., the portions of the signal whose point to point changes are less than an arbitrarily small amount) of the inspired signal and averages the signal values at these flat sections to derive the inspired plateau value IP. The monitor uses IP (1) to set the baseline condition for the blip bar and, (2) as discussed below, as part of the breath qualification algorithm.

In order to provide a semi-quantitative output via the blip bar, the filtered and digitized detector module voltage output signal is converted to a signal that varies in a known relation to the carbon dioxide concentration in the airway sensor. According to Lambert-Beer's law, the concentration of carbon dioxide in the optical path between light source and photodetector is proportional to the logarithm of the ratio of the intensity of the light received by the photodetector in the absence of carbon dioxide to the intensity of the light received by the photodetector in the presence of carbon dioxide. By assuming that the concentration of carbon dioxide in inspired room air is negligible, a look-up table can be generated to relate photodetector output taken from the A/D converter (i.e., light intensity at the photodetector) to partial pressure of carbon dioxide in the airway sensor.

In order to avoid floating point arithmetic, instead of the natural logarithm called for by the Lambert-Beer's equation, the preferred embodiment employs a scaled logarithm of the digitized voltage signal ("slog(v)") based on the input range (1 to 1023—the range of the A/D converter) and the output range (0 to 32,767—a 16 bit integer) as follows:

$$slog(v) = \frac{32{,}767 \ln(v)}{\ln(1023)}$$

Values of slog(v) for the range of expected voltage values are stored in a look-up table in the monitor. Assuming that the carbon dioxide concentration in inspired air is negligible, the carbon dioxide concentration in expired air at any given time is theoretically proportional to the difference between the values of the inspired plateau slog(IP) and instantaneous slog(v)$_i$. In fact, system nonlinearities require the use of an empirically derived quadratic equation to relate the slog(v) values to actual carbon dioxide concentration. The value derived from this quadratic relationship is used to activate the blip bar display, as discussed below.

The preferred embodiment employs breath detection and breath qualification algorithms to distinguish real breaths from artifact and noise before the monitor begins displaying carbon dioxide concentration on the blip bar, however. The breath detection algorithm establishes a threshold for identifying carbon dioxide concentration peaks and troughs. The monitor maintains a history in a memory buffer of the four most recent waveform amplitude values, where waveform amplitude is defined as one-half the difference between the peak waveform value $Slog(V)_{MAX}$ (corresponding to an inspiration, i.e., negligible carbon dioxide concentration) and the trough waveform voltage value $slog(v)_{MIN}$ (corresponding to an exhalation). The initial value $AMP_{INIT}$ of each of the four stored waveform amplitudes is an arbitrary value greater than the system's characteristic noise.

The monitor computes a threshold value T by averaging the four most recent waveform amplitudes. The next $slog(v)_{MAX}$ must exceed T, and the following $Slog(v)_{MIN}$ must drop below T, in order for that section of the slog(v) signal waveform to be "detected" as a likely breath.

After the monitor detects a waveform cycle that is likely to be a breath, the waveform must be qualified as a breath. The monitor's breath qualification algorithm has two steps. First, the monitor computes the waveform cycle period P, the inspired waveform period $P_{IN}$, and the expired waveform period $P_{EX}$. The monitor rejects values of P, $P_{IN}$ and $P_{EX}$ that are too low or too high to be actual breaths. In the preferred embodiment, P, and $P_{EX}$ must correspond to an instrument operating range of 3 breaths/min. to 100 breaths/min.

For the second breath qualification criterion, the monitor looks to see if the inspired plateau digitized voltage value IP discussed above is greater than an arbitrary minimum. If it is not, the monitor will increase the power of the light source (if it is not already at maximum power) in an effort to raise the level of the signal above the expected level of background noise.

Once a breath is detected and qualified, the monitor begins mapping the calculated carbon dioxide concentration values onto the blip bar. Each blip bar segment represents a range of carbon dioxide concentrations. Because some of the system's compenents are temperature sensitive, however, the mapping must be a function of the ambient temperature. In the preferred embodiment, the monitor uses nine different look-up tables-each corresponding to a different temperature subrange within the overall operating temperature range of the system (0–40 deg. C)—to relate the computed carbon dioxide concentration to the number of segments illuminated. In this way, the relationship between blip bar display and actual carbon dioxide concentration remains substantially constant at any temperature within the recommended operating range. The mapping continues for all subsequently computed carbon dioxide concentration values unless and until the apnea alarm triggers.

Also, after a breath is detected and qualified, the monitor stores one-half the difference between the current $slog(v)_{MAX}$ and $slog(v)_{MIN}$ values in memory in place of the oldest of the stored waveform amplitudes. The monitor will then compute a new value of T for use in the detection of the next likely breath. This updating of the amplitude and threshold values occurs after each qualified breath. Finally, qualification of a new breath resets the apnea alarm clock.

Until a new breath is qualified, the stored waveform amplitude values (and the value of T) remain unchanged for the duration of a time-out period defined as twice the period P of the most recent qualified breath cycle, as discussed below. After a period equal to 2*P has passed, the monitor replaces the oldest of the stored waveform amplitudes with $AMP_{INIT}$ and recomputes T. If no likely breaths are detected and qualified for a second period equal to 2*P, then the monitor replaces the next oldest stored waveform amplitude with $AMP_{INIT}$ and recomputes T. The process repeats until all four waveform amplitude memory slots store the value $AMP_{INIT}$, in which case the value of T is $AMP_{INIT}$ as well.

If the monitor fails to qualify any breaths for the duration of an arbitrary apnea alarm period, the monitor alarms (preferably both audibly and visually) to indicate apnea, or the cessation of breathing by the patient, and the blip bar display enters a "breath search" mode in which the LED segments are lit in a moving pattern unlike that of a breath. In the preferred embodiment, the apnea alarm period is 20 seconds. An alarm condition resets the amplitude and threshold parameters to their initial conditions.

As will be understood by those familiar with the art, the present invention may be embodied in other specific forms without departing from the spirit or essential characteristics thereof. For example, the inner diameter of the patient port 13 of airway sensor 4 is preferably equal to the outer diameter of the patient's endotracheal tube. In addition, changes in the length of the optical path could be signaled to the monitor using a coded resistor with the adapter in the manner disclosed in U.S. Pat. No. 4,621,643.

Accordingly, the disclosure of the preferred embodiment of the invention is intended to be illustrative, but not limiting, of the scope of the invention which is set forth in the following claims.

What is claimed is:

1. A sensor system for measuring a constituent gas in the breaths of a patient, the system comprising:
   an airway sensor comprising
      a disposable sensor body defining a gas inlet, a gas outlet, and a gas passageway between the gas inlet and the gas outlet, first and second optical ports in the sensor body defining an optical path across the gas passageway, and
      a light source affixed to the sensor body in alignment with the first optical port; and
   a detector module comprising
   electrical conductor means,
   a photodetector communicating with the electrical conductor means,
   first electrical contact means communicating with the electrical conductor means, and
   first means for removably coupling the detector module to the airway sensor to place the photodetector in alignment with the second optical port and to provide electrical communication between the first electrical contact means and the light source.

2. The sensor system of claim 1 comprising optically transmissive membranes disposed in the first and second optical ports.

3. The sensor system of claim 1 in which the gas inlet comprises means for attaching to an endotracheal tube.

4. The sensor system of claim 1 wherein the airway sensor further comprises second means for attaching the detector module to the airway sensor, the second means for attaching comprising second electrical contact means extending from the light source and terminating at a predetermined position outside of the sensor body housing.

5. The sensor system of claim 4 wherein the predetermined position outside the sensor body comprises a surface extending from the sensor body.

6. The sensor system of claim 4 wherein the predetermined position on the sensor body comprises a surface extending substantially tangentially from a cylindrical surface on the sensor body.

7. The sensor system of claim 4 wherein the second means for attaching further comprises an attachment member extending from the sensor body at a position adjacent to the first optical port.

8. The sensor system of claim 7 wherein the first means for attaching comprises mechanical attachment means for placing the first and second electrical contact means in electrical communication when the mechanical attachment means mates with the attachment member extending from the sensor body.

9. The method of claim 1 wherein the light source is located within a casing that is sonically welded to the sensor body housing.

10. A respiratory carbon dioxide detection system comprising:
   a disposable airway sensor comprising a sensor body housing defining a gas inlet, a gas outlet, and a gas passageway between the gas inlet and the gas outlet, first and second optical ports in the sensor body defining an optical path across the gas passageway, and a light source mounted in the sensor body in alignment with the first optical port;
   a detector module comprising electrical conductor means, a photodetector communicating with the electrical conductor means, electrical contact means communicating with the electrical conductor means, and means for removably coupling the detector module to the airway sensor to place the photodetector in alignment with the second optical port and to provide electrical communication between the electrical contact means and the light source; and
   a monitor communicating with the detector module electrical conductor means, the monitor having means for computing the carbon dioxide concentration of the gas in the optical path of the airway sensor and for displaying the carbon dioxide concentration, the monitor also having means for pulsing the light source to compensate for DC drift of the photodetector.

11. The system of claim 10 in which the display comprises a blip bar.

12. The system of claim 11 in which the blip bar comprises a plurality of separate light sources.

13. The method of claim 10 wherein the light source is pulsed to about 36.5 Hz.

14. An airway sensor for use in a system for measuring a constituent gas in the breaths of a patient, the airway sensor comprising:
   a disposable sensor body defining a gas inlet, a gas outlet, and a gas passageway between the gas inlet and the gas outlet, the sensor body having a housing defining an interior and an exterior;
   first and second optical ports in the sensor body for defining an optical path across the gas passageway;
   a light source permanently affixed to the sensor body in alignment with the first optical port; and
   means for removably coupling the light source to a power source, the means for connecting comprising electrical contact means extending from the light source and terminating outside of the sensor body housing.

15. The airway sensor of claim 14 wherein the electrical contact means extend from the light source to a predetermined position outside of the sensor body housing, and the predetermined position outside the sensor body comprises a surface extending from the sensor body.

16. The airway sensor of claim 14 wherein the predetermined position on the sensor body comprises a surface extending substantially tangentially from a cylindrical surface on the sensor body.

17. The airway sensor of claim 14 further comprising means for attaching a photodetector to the sensor body in alignment with the second optical port, the means for attaching comprising an attachment member extending from the sensor body at a position adjacent to the first optical port.

18. The airway sensor of claim 17 wherein the attachment member comprises lip means extending radially from the first optical port.

19. The airway sensor of claim 17 wherein the means for attaching further comprises stop means for aligning a photodetector with the second optical port.

20. The airway sensor of claim 19 wherein the stop means comprises a wall partially surrounding the second optical port.

21. A method of monitoring the level of carbon dioxide in air, the method comprising the following steps:
connecting a disposable airway sensor to a source of air, the airway sensor comprising, within a housing, a gas inlet, a gas outlet, a gas passageway, first and second optical ports, and a light source, the light source being affixed to the airway sensor housing;

removably coupling a detector module to the airway sensor, the detector module comprising a photodetector and means for attaching the detector module to the airway sensor housing such that the photodetector is aligned with the optical ports of the airway sensor;

passing air through the gas passageway;

monitoring the carbon dioxide content of air passing through the gas passageway by detecting the absorption of radiation from the light source; and removing the airway sensor, including the light source, from the detector module and disposing of the airway sensor.

22. The method of claim 21 wherein the step of attaching comprises snapping the detector module into alignment with the airway sensor such that contacts on the detector module contact light source wires extending from the airway sensor housing.

23. The method of claim 21 further comprising the step of sonically welding a casing to the airway sensor housing, the light source being held in the casing.

* * * * *